US006168809B1

(12) United States Patent
De Lacharriere et al.

(10) Patent No.: US 6,168,809 B1
(45) Date of Patent: *Jan. 2, 2001

(54) ALKALINE-EARTH METAL SALT FOR THE TREATMENT OF OCULAR OR PALPEBRAL PRURITUS AND DYSESTHESIA

(75) Inventors: Olivier De Lacharriere, Paris; Lionel Breton, Versailles, both of (FR)

(73) Assignee: Societe l'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/630,325

(22) Filed: Apr. 10, 1996

(30) Foreign Application Priority Data

Apr. 10, 1995 (FR) .................................................. 95-04266

(51) Int. Cl.⁷ ....................................................... A62K 33/14
(52) U.S. Cl. .......................... 424/677; 424/665; 514/912
(58) Field of Search ...................................... 424/665, 677; 514/912

(56) References Cited

U.S. PATENT DOCUMENTS

| 3,772,431 | 11/1973 | Mlkvy et al. . |
|---|---|---|
| 3,888,976 | 6/1975 | Mlkvy et al. . |
| 4,477,439 | 10/1984 | D'Alelio . |
| 4,943,432 | * 7/1990 | Biener ................................. 424/647 |
| 4,980,184 | 12/1990 | Gordon . |
| 4,986,981 | 1/1991 | Glace et al. . |
| 5,047,409 | 9/1991 | Di Schiena et al. . |
| 5,079,010 | 1/1992 | Natterer . |
| 5,091,171 | 2/1992 | Yu et al. . |
| 5,202,130 | 4/1993 | Grant et al. . |
| 5,328,701 | 7/1994 | Richmond et al. . |

FOREIGN PATENT DOCUMENTS

| 3338957 | 5/1985 | (DE) . |
|---|---|---|
| 0280692 | 7/1990 | (DE) . |
| 0297062 | 1/1992 | (DE) . |
| 0217975 | 4/1987 | (EP) . |
| 0 401 503 | 4/1990 | (EP) . |
| 0439640 | 8/1991 | (EP) . |
| 0451300 | 10/1991 | (EP) . |
| 0459890 | 12/1991 | (EP) . |
| 0 522 808 | 7/1992 | (EP) . |
| 0586929 | 3/1994 | (EP) . |
| 5394 | 10/1967 | (FR) . |
| 2184890 | 6/1978 | (FR) . |
| 2271774 | 4/1994 | (GB) . |
| WO 83/01252 | 4/1983 | (WO) . |
| WO87/01935 | 10/1986 | (WO) . |
| WO93/01165 | 7/1992 | (WO) . |
| WO93/14084 | 7/1993 | (WO) . |
| 93/18747 | 9/1993 | (WO) . |
| 94/13305 | 6/1994 | (WO) . |
| WO 96/19184 | 6/1996 | (WO) . |

OTHER PUBLICATIONS

*Cosmetic Counter*, vol. 109, Oct. 1994.
*Nordia Briefs*, "A Salt–Containing Cream for Dry Skin", No. 484, Jan. 1978.
*The United States Pharmacopeia*, "Alumina/Drug Substances and Dosage Form", pp20 and 22 (1975).
Maison G. deNavarre, *The Chemistry and Manufacture of Cosmetics*, 2nd Ed. vol. IV, p1261 (1975).
Alexander A. Fisher, "Irritant Reactions from Topical Urea Preparations Used for Dry Skin Advantages of a Urea–Free 'Dead Sea Salt' Cream", *Current Contact News*, vol. 18, pp761–772 (1976).
Rajadhyaksha, *Chemical Abstracts*, vol. 107, 1987 #223281.
Di Schiena, *Chemical Abstracts*, vol. 106, 1987, #107768.
Smith et al., *Chemical Abstracts*, vol. 114, 1991, #206554.
Dufetel et al., *Chemical Abstracts*, vol. 116, 1992, #135998.
S.M. Moussaoui et al, *Br. J. Pharmacol.*, "A non–peptide $NK_1$–receptor antagonist, RP 67580, inhibits neurogenic inflammation postsynaptically", vol. 109, No. 1, 1993, pp 259–265.
J. Wallengren, *Br. J. Dermatol.*, "Substance P antagonist inhibits immediate and delayed type cutaneous hypersensitivity reactions", vol. 124, No. 4, 1991, pp 324–328.
J. Wallengren et al, *Contact Dermatitis*, "Some neuropeptides as modulators of experimental contact allergy", vol. 19, No. 5, 1988, pp 351–354.
T. Lotti et al, *J. Am. Acad. Dermatol.*, "Treatment of aquagenic pruritus with topical capsaicin cream", vol. 30. No. 2PT1, Feb. 1994, pp 232–235.
T. Sakurada et al, *Brain Res.*, "A selective and extremely potent antagonist of the neurokinin–1 receptor", vol. 593, No. 2, 1992, pp 319–322.
K. Folkers et al, *Proc. Natl. Acad. Sci. USA*, "Spantide II, an effective tachykinin antagonist having high potency", vol. 87, No. 12, 1990, pp 4833–4855.
Jancso–Gabor, "Action of rare earth metal complexes on neurogenic as well as on bradykinin–induced inflammation", *J. Pharm. Pharmac.*,22:366–371 (1970).
"La peau sensible, un authentique syndrome clinique", *Le Quotidien de Medecin*, No. 5747, Dec. 6, 1995; Cosmetologie, *Therapeutique*, No. 1511, Dec. 17, 1995.

(List continued on next page.)

Primary Examiner—Zohreh Fay
(74) Attorney, Agent, or Firm—Burns, Doane, Swecker & Mathis, L.L.P.

(57) ABSTRACT

The invention relates to the use of an alkaline-earth metal salt in or for the preparation of a cosmetic or pharmaceutical composition, especially for topical application, for treating ocular or palpebral pruritus and/or ocular or palpebral dysesthesia. The cosmetic composition can be used for applying make-up to or removing make-up from sensitive eyes.

43 Claims, No Drawings

OTHER PUBLICATIONS

Uy Dong Sohn et al, "Agonist–Independent, Muscle–Type–Specific Signal Transduction Pathways in Cat Esophageal and Lower Esophageal Sphincter Circular Smooth Muscle", *J. of Pharmacology & Experimetal Therapeutics*, 273:481–491 (1995).

Mitsuo Ishizawa, "Contractile Responses of Longitudinal Muscle Strip to 5–HT and Influences of Divalent Cations in the Guinea–Pig Isolated Colon", *J. Smooth Muscle Res.*, 30:65–72 (1994).

H. Goodman, *Cosmetic Dermatology*, First Edition, Fourth Impression, p. 181 (1936).

*Martindale*, The Extra Pharmacopoeia, Twenty–seventh Edition, The Pharmaceutical Press, London, pp 219, 1775 and 1814 (1977).

*McGraw–Hill Dictionary of Scientific and Technical Terms*, Fifth Edition, pp 109 and 332.

Sohn et al, Different Receptors Activate a Different Single G–Protein in Esophageal. (Gis) and In LES (Gq) Circular Smooth Muscle, *Gastroenterology*, vol. 104 (1993).

* cited by examiner

ALKALINE-EARTH METAL SALT FOR THE TREATMENT OF OCULAR OR PALPEBRAL PRURITUS AND DYSESTHESIA

The present invention relates to the use of an alkaline-earth metal salt for the preparation of a pharmaceutical composition for treating, especially via the topical route, ocular and/or palpebral pruritus and/or ocular and/or palpebral dysesthesia. It also relates to the use of an alkaline-earth metal salt in a cosmetic composition intended for the care of or for applying make-up to the eyes or to the eyelids as well as to a process for the care of and/or for applying make-up to sensitive eyes.

Some patients very frequently have itching sensations or pruritus and dysesthetic sensations at the level of the eyes and the eyelids without always knowing their precise cause. They may also be pruritus or dysesthetic sensations of allergic origin.

Dysesthetic sensations are understood to mean sensations of burning or of overheating, pricking, formication, discomfort and stabbing pain. These sensations may be combined with reddening.

All these ophthalmic signs may, in addition, be combined with rosacea and optionally with conjunctivitis.

Among the factors which initiate ophthalmic or palpebral prurigenous or dysesthetic crises, there may be mentioned rapid temperature variations, heat and especially exposure to ultraviolet or infrared radiation, relatively low humidity, exposure to violent winds or to air currents (fan, air conditioner), application of surfactants (shampoo), exposure to toxic or irritant vapours (solvents) or to dust, drops or irritant ophthalmological topical drugs, irritant dermatological or cosmetic palpebral topical drugs (alpha-hydroxyacids, retinoids), or the use of some cosmetics even when these are not known to be particularly irritant. Like other factors which initiate ocular or palpebral pruriginous or dysesthetic crises, there should be included, in addition, allergens such as especially pollen, animal hair, acarians and moulds.

Up until now, the pathological mechanism of these signs was poorly known and ocular and/or palpebral dysesthesia was treated with corticoids and also local antiseptics in the form of an ophthalmic ointment or as drops.

Corticoids are relatively effective for reducing the above symptoms but unfortunately they have side effects which are very often detrimental, such as atrophies. Furthermore, they create sensitivity to mycotic or bacterial infections and their kinetics of action is often slow (several minutes to a few hours). Moreover, their chronic use may lead to drug dependence. In addition, their action is not immediate and the dysesthetic sensations last for several minutes.

The need therefore exists for a treatment of ocular and palpebral pruritus and dysesthesia having immediate effect, which does not have the above disadvantages.

The subject of the present invention is precisely the use of one or more alkaline-earth metal salts for treating these conditions.

The Applicant observed that ocular and/or palpebral dysthesthesia was linked to the stimulation of the nerve fibres and to the release, by the sensitive nerve endings, of neuropeptides such as for example substance P and CGRP (Calcitonin Gene Related Peptide) as well as pro-inflammatory mediators liberated as a result of the attachment of certain neuropeptides (especially substance P) onto the mastocyte receptors. These pro-inflammatory mediators are more particularly histamine, heparin, serotonin, interleukin-1 (IL1), interleukin-6 (IL6), interleukin-8 (IL8) and Tumor Necrosis Factor-alpha (TNF-alpha). Recruitment of the neutrophilic white blood cells by certain neuropeptides (especially CGRP) is also involved in this inflammatory process.

No-one had envisaged using, up till now, alkaline-earth metal salts to treat ocular or palpebral pruritus and/or dysesthesia.

Accordingly, the subject of the present invention is the use of at least one salt of at least one alkaline-earth metal for the preparation of a pharmaceutical or dermatological composition for treating ocular or palpebral pruritus and/or ocular or palpebral dysesthesia.

The application of compositions containing one or more salts of one or more alkaline-earth metals to the eyes or the eyelids makes it possible to obtain a marked decrease or even a complete disappearance of the dysesthetic sensations and ocular pruritus; a preventive and curative, soothing and alleviating effect is very rapidly observed, and in any case much more rapidly than with corticoids, on the eyes and the eyelids. In addition, no drug dependence is noted.

By virtue of the alkaline-earth metal salts, it is in addition possible to conceive cosmetic products for sensitive eyes and in particular lotions for removing make-up or for cleaning the eyes, make-up products for sensitive eyes and especially eye shadows, mascaras, pencils or eye liners for sensitive eyes.

Accordingly, the subject of the invention is also the use of at least one salt of at least one alkaline-earth metal in a cosmetic composition containing a cosmetically acceptable medium, intended for sensitive eyes.

The subject of the invention is thus a process for the care of or for applying make-up to sensitive eyes and a process for the treatment of sensitive eyes, which consists in applying, to the eyelids, the eyelashes or under the sensitive eyes, a composition containing at least one salt of at least one alkaline-earth metal in a cosmetically or pharmaceutically acceptable medium.

The object of the invention is also a cosmetic, pharmaceutical or dermatological composition for sensitive eyes containing, in a cosmetically or pharmaceutically or dermatologically acceptable medium, at least one alkaline-earth metal and at least one neuropeptide antagonist and/or at least one inflammation mediator antagonist.

The composition of the invention contains a cosmetically, pharmaceutically or dermatologically acceptable medium, that is to say a medium compatible with the skin and the eyes. The composition containing the salt(s) of (an) alkaline-earth metal(s) is applied especially via the topical route.

As alkaline-earth metal salts which can be used in the invention, there may be mentioned barium, calcium, magnesium, strontium and/or beryllium salts. These salts may be for example carbonates, bicarbonates, sulphates, glycerophosphates, borates, chlorides, nitrates, acetates, hydroxides, persulphates as well as salts of $\alpha$-hydroxyacids (citrates, tartrates, lactates, maleates) or of fruit acids, or alternatively aminoacid salts (aspartate, arginate, glycocholate, fumarate) or fatty acid salts (palmitate, oleate, caseinate, behenate). For example, the salt is chosen from calcium or magnesium nitrate, calcium or magnesium borate, calcium or magnesium chloride, calcium or magnesium sulphate and calcium or magnesium acetate. Advantageously, the salt is a magnesium or better still a strontium salt and in particular a chloride or a nitrate.

The Applicant found surprisingly that the ability of the alkaline-earth metal salts to treat sensitive eyes was due especially to the fact that these salts were inhibitors of the release of TNF-alpha, or even inhibitors of the release of neuropeptides such as CGRP and substance P.

In the compositions according to the invention, the alkaline-earth metal salts are used preferably in a quantity ranging from 0.01 to 20% of the total weight of the composition, and in particular in a quantity ranging from 0.1 to 15% of the total weight of the composition or even better from 0.5% to 8%.

The compositions according to the invention can be provided in any gallenic form normally used for a topical application; the composition can be provided especially in the form of aqueous, aqueous-alcoholic or oily solutions, or of lotion or serum type dispersions, of emulsions of liquid or semiliquid consistency of the milk type, which are obtained by dispersing a fatty phase in an aqueous phase (O/W) or conversely (W/O), or of suspensions or emulsions of soft, semisolid or solid consistency of the cream or aqueous or anhydrous gel type, of microemulsions, of microcapsules, of microparticles, of vesicular dispersions of the ionic and/or nonionic type, of compacted or cast powders. These compositions are prepared according to the customary methods. They are essentially intended for topical application.

For a topical application for therapeutic purposes, the compositions are provided especially in the form of a gel, cream, ointment for the treatment of palpebral pruritus and/or dysesthesia and in the form of a collyrium or of an ocular washing solution for the treatment of ocular pruritus and/or dysesthesia.

For a cosmetic application, compositions may especially consist of creams for the care or protection of sensitive eyes, of milks or lotions for cleaning or removing make-up from sensitive eyes, of make-up products for the eyes, especially sensitive eyes, such as pencils, mascaras, eye liners, eye shadows.

The quantities of the various constituents of the compositions according to the invention are those conventionally used in the fields considered.

When the composition of the invention is an emulsion, the proportion of the fatty phase may range from 5% to 80% by weight, and preferably from 5% to 50% by weight relative to the total weight of the composition. The oils, emulsifiers and coemulsifiers used in the composition in the form of an emulsion are chosen from those conventionally used in the cosmetic and dermatological fields. The emulsifier and the coemulsifier are present in the composition in a proportion ranging from 0.3% to 30% by weight, preferably from 0.5 to 20% by weight relative to the total weight of the composition. The emulsion may, in addition, contain lipid vesicles.

When the composition is a solution or an oily gel, the quantity of oil may be as high as 90% by weight of the total weight of the composition.

In a known manner, the composition of the invention may also contain adjuvants which are customary in the fields considered, such as hydrophilic or lipophilic gelling agents, hydrophilic or lipophilic active agents, preservatives, antioxidants, solvents, perfumes, fillers, sunscreens, odour absorbers, pigments and colouring matter. The quantities of these various adjuvants are those conventionally used in the fields considered, for example from 0.01% to 10% of the total weight of the composition. These adjuvants, depending on their nature, can be introduced in the fatty phase, in the aqueous phase and/or in the lipid spherules.

As oils which can be used in the invention, there may be mentioned mineral oils (liquid paraffin), vegetable oils (liquid fraction of shea butter, sunflower oil), animal oils (perhydrosqualene), synthetic oils (Purcellin oil), silicone oils (cyclomethicone) and fluorinated oils (perfluoropolyethers). It is also possible to use fatty alcohols, fatty acids (stearic acid) or alternatively waxes (paraffin, carnauba, beeswax).

As emulsifiers which can be used in the invention, there may be mentioned for example glycerol stearate, polysorbate 60 or 80 and the PEG-G/PEG-32/Glycol Stearate sold under the name Tefose® 63 by the company Gattefosse.

As hydrophilic gelling agents, there may be mentioned carboxyvinyl polymers (carbomer), acrylic copolymers such as acrylate/alkyl acrylate copolymers, polyacrylamides, polysaccharides such as hydroxypropyl cellulose, natural gums and clays, and, as lipophilic gelling agents, there may be mentioned modified clays such as bentones, fatty acid metal salts such as aluminium stearates, hydrophobic silica, polyethylenes and ethyl cellulose.

As hydrophilic active agents, it is possible to use proteins or protein hydrolysates, amino acids, polyols, urea, allantoin, sugars and sugar derivatives, water-soluble vitamins, starch, bacterial or plant extracts, especially of Aloe vera.

As lipophilic active agents, it is possible to use tocopherol (vitamin E) and its derivatives, retinol (vitamin A) and its derivatives, essential fatty acids, ceramides, essential oils.

It is also possible to combine the alkaline-earth metal salts with active agents, especially cicatrizing agents (for example vitamin $B_{12}$), antiseptics (for example boric acid), antiallergic agents (for example sodium chromoglycate), antiviral agents (for example acyclovir), anaesthetics (for example lidocaine hydrochloride and its derivatives), non-steroidal anti-inflammory agents (for example indomethacin), antagonists of neuropeptides (antagonists of substance P, of CGRP), and antagonists of histamine, of interleukin (especially IL1) or of TNFα (Tumor Necrosis Factor-α) as well as a small quantity of corticoids, these active agents being different from the alkaline-earth metal salts.

The Applicant defines a neuropeptide or inflammation mediator antagonist as any molecule of organic or inorganic origin capable of producing inhibition of the receptor binding of the neuropeptide or mediator considered or of producing inhibition of the synthesis and/or release of this neuropeptide or mediator by the sensitive nerve fibres.

Advantageously, the neuropeptide antagonists are receptor antagonists.

Preferably, the neuropeptide antagonist(s) are chosen from antagonists of substance P and antagonists of CGRP, especially receptor antagonists.

CGRP 8-37, an anti-CGRP antibody, can be used in the invention, for example, as CGRP antagonist.

By way of example, the neuropeptide antagonists and the inflammation mediator antagonists can be used in a quantity representing from 0.000001 to 10% of the total weight of the composition and better still from 0.0001 to 5%.

As inflammation mediator antagonists which can be used in the invention, there may be mentioned diethylenediamine derivatives such as cinnarizine, cyclizine; aminopropane derivatives (dexchlorpheniramine, tripolidine); phenothiazine derivatives (alimemazine, promethazine); auranofin; lisophyline; A802715; sulfasalazine; cetirizine HCl; loratidine; esbatine; setastine HCl;

Tests have demonstrated the activity of various strontium salts as substance P antagonists with reference to Spantide II, known as a substance P antagonist, and in comparison with another alkaline-earth metal salt, calcium nitrate.

The test consisted in determining the activity of various compounds on the release of substance P, which is caused by antidromic stimulation of the sciatic nerve. This release is visualized by staining with a stain (Evans blue). The greater the quantity of substance P released, the more intense the colour. In other words, the greater the inhibitory effect of the substance P antagonist on this release, the less intense the colour.

The results are presented in the tables below:

TABLE 1

|  | Control vehicle | Spantide II 30 nmol | $Sr(NO_3)_2$ 1 μmol | $SrCl_2$ 1 μmol | $Ca(NO_3)_2$ 1 μmol |
|---|---|---|---|---|---|
| μg/ml of Evans blue | 8.19 ± 0.83 | 4.35 ± 0.46 | 4.84 ± 0.6 | 5.13 ± 0.9 | 11.25 ± 1.77 |
| % inhibition relative to the control | — | 47% | 41% | 37% | — |
| Statiatics | — | $p < 0.01$ | $p < 0.05$ | $p < 0.05$ | not significant |

It is evident from this table that the strontium salts have a substantial inhibitory activity on the release of substance P whereas the calcium salt, at the same concentration, has no activity at all.

TABLE 2

|  | Control vehicle | Spantide II 30 nmol | $Sr(NO_3)_2$ 3 μmol | $SrCl_2$ 1 μmol | $Ca(NO_3)_2$ 10 μmol |
|---|---|---|---|---|---|
| μg/ml of Evans blue | 6.26 ± 1.09 | 3.63 ± 0.69 | 1.80 ± 0.68 | 2.71 ± 0.67 | 8.45 ± 1.55 |
| % inhibition relative to the control | — | 42% | 71% | 57% | — |
| Statiatics | — | $p < 0.05$ | $p < 0.001$ | $p < 0.01$ | not significant |

It is evident from this table that the strontium salts have a substantial inhibitory activity on the release of substance P whereas the calcium salt has no activity at all, even at a higher concentration level.

The following test makes it possible to show that the alkaline-earth metal salts and more particularly magnesium, strontium or calcium chloride as well as strontium nitrate are inhibitors of TNF-alpha.

This test is performed on human monocytes (line U937) stimulated by a phorbol ester (PMA) according to the method described by Schindler et al. (Correlations and interactions in the production of interleukin-6 (IL-6), IL-1, and Tumor Necrosis Factor (TNF) in human blood mononuclear cells: IL-6 suppresses IL-1 and TNF. Blood 75: 40–47 (1990)).

The phorbol ester (PMA) naturally stimulates the synthesis and/or the secretion of TNF-alpha by human monocytes in culture.

The activity of the molecules is evaluated according to their capacity to reduce or even suppress this TNF-alpha secretion.

The cells (monocytes) are incubated in the presence of PMA at the concentration of 10 nM for 48 hours at 37° C. The quantities of TNF-alpha secreted are quantified by immunoenzymatic assay (ECA) with the aid of commercially available kits.

Each molecule is tested at 3 different concentrations ($10^{-5}$, $10^{-4}$ and $10^{-3}$ M) and in each experiment, a reference molecule (dexamethasone) is studied at 7 concentrations as internal standard.

The results are expressed as percentage of inhibition relative to the positive control (without test molecule) after subtracting the background noise. A recapitulative table groups together the mean inhibitory effects obtained with the compounds. (The results are expressed as % inhibition; they are the mean of 3 measurements).

The $IC_{50}$ value (50% decrease in the secretion, caused by PMA) is calculated, for the reference molecule, from the competition curve according to a nonlinear regression model.

TABLE

| Test | Compounds | $10^{-5}$M | $10^{-4}$M | $10^{-3}$M | Reference | $IC_{50}$ |
|---|---|---|---|---|---|---|
| Secretion of TNF-alpha induced by PMA | $SrCl_2 7H2O$ | 14 | — | 54 | dexamethasone | $4 \times 10^{-9}$M |
|  | $M_gCl_2$ | — | 12 | 70 |  |  |
|  | $CaCL_2.7H_2O$ | 19 | 22 | 67 |  |  |
|  | $Sr(NO_3)_2$ | — | 28 | 75 |  |  |

It is observed that the inhibition of TNF-alpha increases with the salt concentration.

The following examples illustrate the invention. In these examples, the proportions indicated are percentages by weight.

EXAMPLE 1

Collyrium

| Strontium chloride | 3% |
|---|---|
| Excipient: Sodium chloride Sodium borate Polysorbate 80 Boric acid Water | qs 100% |

EXAMPLE 2

Ointment

| Magnesium nitrate | 5% |
|---|---|
| Excipient: Benzalkonium chloride Sodium edetate D-mannitol Carbomer Sodium hydroxide Water | qs 100% |

EXAMPLE 3

Solution

| Calcium borate | 2% |
|---|---|
| Excipient: |  |
| Boric acid | 5% |
| Sodium chloride | 0.3% |

|  |  |
|---|---|
| Phenylmercuric borate | 0.5% |
| Water | qs 100% |

EXAMPLES 4 AND 5

Ointments

These examples differ from Example 2 in the addition of 0.1% sendide and loratidin respectively.

EXAMPLE 6

This example differs from Example 1 in the use of 5% strontium nitrate.

What is claimed is:

1. A method of treating sensitive eyes comprising applying to the eyelids, the eye lashes or under the eyes a cosmetic composition comprising an effective amount of at least one strontium salt contained in a cosmetically or dermatologically acceptable medium; wherein the composition is capable of inhibition of the binding receptor of substance P, inhibition of the synthesis and/or the release of substance P by the sensitive nerve fibers, or a combination thereof.

2. A method for the care of or for applying makeup to sensitive eyes, comprising applying to the eyelids, the eye lashes or the skin under the eyes, a cosmetic composition comprising an effective amount of at least one strontium salt contained in a cosmetically acceptable medium; wherein the composition is capable of inhibition of the binding receptor of substance P, inhibition of the synthesis and/or the release of substance P by the sensitive nerve fibers, or a combination thereof.

3. A cosmetic composition suitable to topical treatment of sensitive eyes which contains in a cosmetically acceptable medium an effective amount of at least one strontium salt and at least one neuropeptide antagonists and/or at least one inflammation mediator antagonist; wherein the composition is capable of inhibition of the binding receptor of substance P, inhibition of the synthesis and/or the release of substance P by the sensitive nerve fibers, or a combination thereof.

4. The method of claim 1, wherein said effective amount of at least one strontium salt is an amount that inhibits dysaesthetic sensations associated with sensitive eyes.

5. The method of claim 4, wherein said sensations include burning, overheating, prickling, formication, discomfort, pain, and itching.

6. The method of claim 2, wherein said effective amount of at least one strontium salt is an amount that inhibits dysaesthetic sensations associated with sensitive eyes.

7. The method of claim 5, wherein said sensations include burning, overheating, prickling, formication, discomfort, pain, and itching.

8. The cosmetic composition of claim 3, wherein said effective amount of at least one strontium salt is an amount that inhibits the dysaesthetic sensations associated with sensitive eyes.

9. The cosmetic composition of claim 8, wherein said symptoms include burning, overheating, prickling, formication, discomfort, pain, and itching.

10. The method of claim 1, wherein the strontium salt is selected from the group consisting of strontium chlorides, carbonates, borates, nitrates, acetates, hydroxides, sulfates, fruit acids and amino acids of strontium.

11. The method of claim 1, wherein the strontium salt is strontium chloride or strontium nitrate.

12. The method of claim 1, wherein the administered composition additionally comprises another alkaline-earth metal salt selected from the group consisting of magnesium salts, calcium salts, barium salts, and beryllium salts.

13. The method of claim 12, wherein the other alkaline-earth metal salt is selected from the group consisting of calcium nitrate, magnesium nitrate, calcium borate, magnesium borate, calcium chloride, magnesium chloride, calcium acetate, and magnesium acetate.

14. The method of claim 1, wherein the amount of strontium salt in the composition ranges from about 0.01 to 20% by weight relative to the total weight of the composition.

15. The method of claim 1, wherein the amount of strontium salt in the composition ranges from 0.5 to 8% by weight relative to the total weight of the composition.

16. The method according to claim 1, wherein the composition contains in addition at least one active ingredient selected from the group consisting of proteins, protein hydrolysates, amino acids, polyols, urea, sugars, sugar derivatives, vitamins, starches, plant extracts, ceramides, essential oils and sunscreens.

17. The method according to claim 1, wherein the composition contains in addition at least one other agent selected from the group consisting of cicatrizing agents, antiseptics, anti-allergic agents, anesthetics, anti-viral agents, non-steroidal anti-inflammatory agents, neuropeptide antagonists and inflammation mediator antagonists.

18. The method according to claim 1, wherein the administered composition further comprises at least one substance P antagonist or CGRP antagonist.

19. The method according to claim 17, wherein the neuropeptide antagonist is a receptor antagonist.

20. The method according to claim 1, wherein the administered composition is selected from the group consisting of aqueous, oily and aqueous-alcoholic solutions, water-in-oil emulsions, oil-in-water emulsions, microemulsions, aqueous gels, anhydrous gels, serums, dispersions of vesicles, microcapsules and microparticles, and compacted or cast powders.

21. The method according to claim 1, wherein the administered composition is in the form of a gel, cream or ointment.

22. The method according to claim 1, wherein the administered composition is in the form of a collyrium.

23. A method according to claim 1, wherein the cosmetic composition further comprises an alkaline-earth metal salt which is selected from the group consisting of chlorides, carbonates, borates, nitrates, acetates, hydroxides, sulfates, fruit acids and amino acids of barium, calcium, magnesium, and beryllium.

24. A method according to claim 23, wherein the alkaline-earth metal salt is selected from the group consisting of calcium nitrate, magnesium nitrate, calcium borate, magnesium borate, calcium chloride, magnesium chloride, calcium acetate and magnesium acetate.

25. A method according to claim 23, wherein the alkaline-earth metal salt is a magnesium salt.

26. A method according to claim 2, wherein said strontium salt is strontium chloride or strontium nitrate.

27. A method according to claim 2, wherein the amount of said strontium salt contained in the composition ranges from 0.01 to 20% by weight relative to the total weight of the composition.

28. A method according to claim 2, wherein the amount of said strontium salt contained in the composition ranges from about 0.5 to 8% by weight relative to the total weight of the composition.

29. A method according to claim 2, wherein the composition contains in addition at least one active agent selected from the group consisting of proteins, protein hydrolysates, amino acids, polyols, urea, sugars, sugar derivatives, vitamins, starches, plant extracts, ceramides, essential oils and sunscreens.

30. A method according to claim 2, wherein the composition contains in addition at least one active agent selected from the group consisting of cicatrizing agents, antiseptics, anti-allergic agents, anesthetics, anti-viral agents, non-steroidal anti-inflammatory agents, neuropeptide antagonists and inflammation mediator antagonists.

31. A method according to claim 2, wherein the administered composition is selected from the group consisting of aqueous, oily and aqueous-alcoholic solutions, water-in-oil emulsions, oil-in-water emulsions, microemulsions, aqueous gels, anhydrous gels, serums, dispersions of vesicles, microcapsules or microparticles, and compacted or cast powders.

32. A method according to claim 2, wherein the administered composition is a gel, cream or ointment.

33. A method according to claim 2, wherein the administered composition is in the form of a collyrium.

34. A composition according to claim 3, wherein the composition further comprises an alkaline-earth metal salt which is selected from the group consisting of chlorides, carbonates, borates, nitrates, acetates, hydroxides, sulfates, fruit acids and amino acids of barium, calcium, magnesium, and beryllium.

35. A composition according to claim 34, wherein said alkaline-earth metal salt is selected from the group consisting of calcium nitrate, magnesium nitrate, calcium borate, magnesium borate, calcium chloride, magnesium chloride, calcium acetate and magnesium acetate.

36. A composition according to claim 3, wherein said strontium salt is strontium chloride or strontium nitrate.

37. A composition according to claim 3, wherein the amount of said strontium salt contained in the composition ranges from 0.5 to 8% by weight relative to the total weight of the composition.

38. A composition according to claim 36, wherein the amount of said strontium salt ranges from about 0.5 to 8% by weight relative to the total weight of the composition.

39. A composition according to claim 3, wherein the composition contains in addition at least one active agent selected from the group consisting of proteins, protein hydrolysates, amino acids, polyols, urea, sugars, sugar derivatives, vitamins, starches, plant extracts, ceramides, essential oils and sunscreens.

40. A composition according to claim 3, wherein the composition contains in addition at least one other agent selected from the group consisting of cicatrizing agents, antiseptics, anti-allergic agents, anesthetics, anti-viral agents, and non-steroidal anti-inflammatory agents.

41. A composition according to claim 3, wherein the neuropeptide antagonist is selected from the group consisting of substance P antagonist and CGRP antagonist.

42. A composition according to claim 3, wherein the neuropeptide antagonist is a receptor antagonist.

43. A composition according to claim 3, wherein the composition is selected from the group consisting of aqueous, oily and aqueous-alcoholic solutions, water-in-oil emulsions, oil-in-water emulsions, microemulsions, aqueous gels, anhydrous gels, serums, dispersions of vesicles, microcapsules or microparticles, and compacted or cast powders.

\* \* \* \* \*